United States Patent
Elibol (10) Patent No.: US 10,132,771 B2
(45) Date of Patent: Nov. 20, 2018

(54) SELF ALIGNED AND SCALABLE NANOGAP POST PROCESSING FOR DNA SEQUENCING

(71) Applicant: Intel Corporation, Santa Clara, CA (US)

(72) Inventor: Oguz H. Elibol, Mountain View, CA (US)

(73) Assignee: Intel Corporation, Santa Clara, CA (US)

( * ) Notice: Subject to any disclaimer, the term of this patent is extended or adjusted under 35 U.S.C. 154(b) by 84 days.

(21) Appl. No.: 15/122,111

(22) PCT Filed: Mar. 28, 2014

(86) PCT No.: PCT/US2014/032210
§ 371 (c)(1),
(2) Date: Aug. 26, 2016

(87) PCT Pub. No.: WO2015/147867
PCT Pub. Date: Oct. 1, 2015

(65) Prior Publication Data
US 2017/0074819 A1    Mar. 16, 2017

(51) Int. Cl.
*G01N 27/28* (2006.01)
*G01N 33/48* (2006.01)
(Continued)

(52) U.S. Cl.
CPC ....... *G01N 27/3278* (2013.01); *C12Q 1/6869* (2013.01); *C23C 14/34* (2013.01);
(Continued)

(58) Field of Classification Search
CPC .. G01N 27/07; G01N 27/3278; G01N 27/128; G01N 27/28; G01N 27/30;
(Continued)

(56) References Cited

U.S. PATENT DOCUMENTS

2010/0267158 A1   10/2010   Chou
2011/0056845 A1   3/2011   Stellacci
(Continued)

OTHER PUBLICATIONS

Intel Corporation, "International Preliminary Report on Patentability", PCT/US2014/032210, (dated Oct. 13, 2016).
(Continued)

*Primary Examiner* — Susan D Leong
(74) *Attorney, Agent, or Firm* — Schwabe, Williamson & Wyatt, P.C.

(57) ABSTRACT

An apparatus including a circuit substrate including a contact in a metal layer; and a transducer including a first electrode deposited on and coupled to a sidewall of the contact and a second electrode coupled to a conductor through which voltage can be applied, wherein the second electrode includes a profile aligned to the sidewall of the contact and separated from the first electrode by a gap. A method including forming a transducer adjacent a contact in a metal layer on a substrate, the transducer including a first electrode disposed on a sidewall of the contact and a second electrode coupled to a conductor through which voltage can be applied, wherein the second electrode includes a profile aligned to the sidewall of the contact and separated from the first electrode by a gap.

22 Claims, 7 Drawing Sheets (51) Int. Cl.
*G01N 27/327* (2006.01)
*C12Q 1/6869* (2018.01)
*C23C 14/34* (2006.01)
*C23C 16/455* (2006.01)
*C23C 18/16* (2006.01)
*G01N 33/487* (2006.01)

(52) U.S. Cl.
CPC .... *C23C 16/45525* (2013.01); *C23C 18/1633* (2013.01); *G01N 33/48721* (2013.01)

(58) Field of Classification Search
CPC .. G01N 27/3273; G01N 27/403; G01N 33/48; G01N 33/48721; C12Q 1/6869; C12Q 1/6874; C23C 14/34; C23C 16/45525; C23C 18/1633
See application file for complete search history.

(56) References Cited

U.S. PATENT DOCUMENTS

| | | |
|---|---|---|
| 2011/0268884 A1 | 11/2011 | Wind et al. |
| 2012/0122715 A1 | 5/2012 | Gao et al. |
| 2013/0186757 A1 | 7/2013 | Reinhart et al. |
| 2013/0281325 A1 | 10/2013 | Elibol et al. |
| 2014/0001055 A1* | 1/2014 | Elibol ................ G01N 27/3277 205/777.5 |

OTHER PUBLICATIONS

Chen, X., et al., "Electrical nanogap devices for biosensing", Materials Today, vol. 13, No. 11, (2010), 28-41.

Davis, B. H., et al., "Sensing DNA with alternating currents using a nanogap sensor embedded in a nanochannel device", Nano Life, vol. 3, No. 1, (2013), 1-15.

Intel Corporation, "International Search Report and Written Opinion", International Application No. PCT/US2014/032210, (dated Dec. 17, 2014), 9 pages.

Kang, S., et al., "Electrochemical Single-Molecule Detection in Aqueous Solution using Self-Aligned Nanogap Transducers", American Chemical Society (ACS) Nano, vol. 7, No. 12, (2013), 10931-10937.

Extended European Search Report for European patent Application No. 14886751.8, dated Sep. 4, 2017, 9 pages.

Lee, Joon Sung et al., Nano Capacitors for Label Free DNA Analysis, Materials Research Society Proceedings, vol. 729, 2002, 6 pages.

* cited by examiner

SELF ALIGNED AND SCALABLE NANOGAP POST PROCESSING FOR DNA SEQUENCING

CROSS-REFERENCE TO RELATED APPLICATION

This patent application is a U.S. National Phase Application under 35 U.S.C. § 371 of International Application No. PCT/US2014/032210, filed Mar. 28, 2014, entitled SELF ALIGNED AND SCALABLE NANOGAP POST PROCESSING FOR DNA SEQUENCING.

FIELD

Electronic nucleic acid sequencing device.

BACKGROUND

The electronic DNA sequencing platform generally requires monolithic integration of electrochemical nanogap transducers on complementary metal oxide semiconductor (CMOS) substrates to achieve ultra dense integration of sensors on substrates. One fabrication technique involves fabricating CMOS substrates without altering the foundry process and removing wafers at an appropriate point in the backend and transferring such wafers to a different clean room for "post processing" to monolithically integrate the transducers. Post processing is done in a different fabrication facility due to the need of using non-conventional materials (such as platinum, gold, diamond, chromium) and non-conventional fabrication processes (such as liftoff, sputter etching). The process of monolithic integration of the nanogap transducers is referred to as "post processing" owing to the wafers having to go through additional processing after leaving the foundry in which the CMOS electronics are fabricated. A current pitch of transducers arrays is less than two microns (μm) with about one million transducers.

DETAILED DESCRIPTION

An apparatus including an integrated circuit substrate comprising a contact and a transducer associated with the contact is disclosed. In another embodiment, an apparatus including an array of contacts and corresponding transducers associated with the contacts is disclosed. Representatively, an apparatus includes an integrated circuit substrate, a device layer and including a contact or contacts in a metal layer such as an ultimate metal layer, and a transducer including a first electrode deposited on and connected to a sidewall of the contact(s) and a second electrode coupled to a conductor through which voltage can be applied, wherein the second electrode includes a profile aligned to the sidewall of the contact(s) and separated from the first electrode by a gap. A method of forming an apparatus including a transducer or an array of transducers is also disclosed. In one embodiment, the method involves a post-processing that will allow the self-aligned monolithic integration of nanogap devices (transducers). The method is used to realize "vertical" nanogaps, in which the devices are self-aligned to respective sidewalls of the metal layer used, for example, in the ultimate metallization of an integrated circuit device fabrication (e.g., CMOS fabrication). The method allows defining critical dimensions (gap size and device footprint) without relying on the resolution and alignment tolerance of the lithography equipment used in the post-processing of the devices. Also, a liftoff process is not used in the definition of any of the critical dimensions of the device. Dead volumes are avoided due to the self-aligned nature of the process and there is no need to introduce an access hole to etch a sacrificial layer and exchange fluid.

Figure 1:
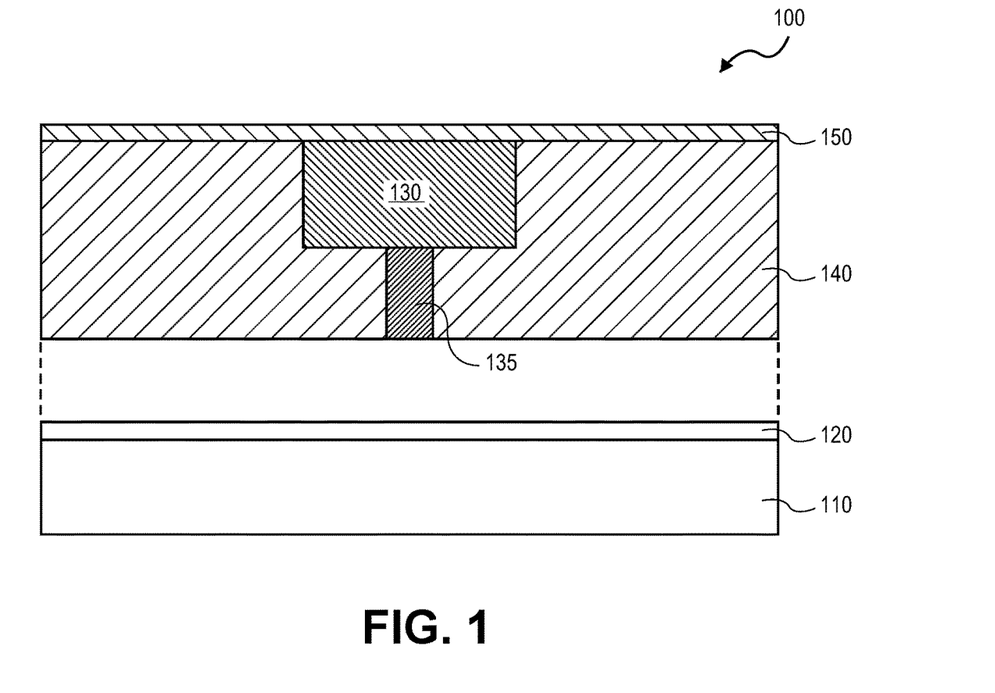
FIG. 1 shows a cross-sectional side view of a portion of an integrated circuit structure including a device layer formed in and on a substrate and metallization including an ultimate metal layer defined as a contact and capped with a capping layer.

FIGS. 1-14 describe an embodiment of a method of forming an integrated circuit device including one or more transducers self-aligned to contacts of an ultimate metal layer of the structure. More specifically, an embodiment of a post-processing method is described. The post processing starts after pulling the wafer out at an appropriate stage of the backend process. Accordingly, the integrated circuit device is formed in or on a substrate such as a wafer and includes devices (e.g., transistor devices) and circuitry (e.g., CMOS) connected through interconnects defined at least in part by metal layers. FIG. 1 shows a cross-sectional side view of a portion of an integrated circuit structure including a device layer formed in and on a substrate and metallization including an ultimate metal layer capped with a capping layer. Referring to FIG. 1, structure 100 includes substrate 110 that is, for example, a single crystal semiconductor substrate (e.g., silicon substrate) or a semiconductor on insulator substrate. In one embodiment, substrate 110 is a portion of a die of a wafer. Substrate 110 includes device layer 120 and representatively a number of metal lines on the device layer. The metal lines and associated conductive vias between the device layer and the lines serve in one aspect as interconnects to bring power to and signals to and from the device layer. FIG. 1 shows ultimate metal layer 130 of, for example, copper or a copper alloy and conductive via 135 to connect ultimate metal layer 130 to an underlying metal layer. In one embodiment, at least a portion of ultimate metal layer 130 is patterned into contacts including opposing side portions that define a thickness of the layer. The opposing side portions of the contacts of ultimate metal layer 130 are surrounded by interlayer dielectric material 140. In the following discussion, ultimate metal layer 130 will interchangeably be described as contact(s) 130. In one embodiment, interlayer dielectric material 140 is silicon nitride. FIG. 1 also shows capping layer 150 on interlayer dielectric material 140 and ultimate metal layer 130. If the post processing is done in the same foundry as the device circuitry or with short time delays, capping layer 150 can be avoided.

Figure 2:
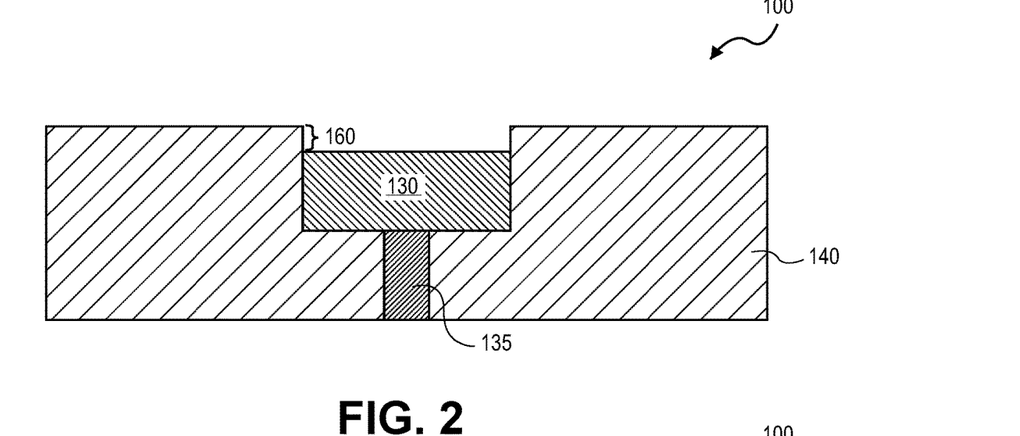
FIG. 2 shows the structure of FIG. 1 following the removal of any capping layer and recessing the contact relative to the adjacent interlayer dielectric.

FIG. 2 shows the structure of FIG. 1 following the removal of any capping layer and forming a recess on top of contact 130. Recess 160 is formed in one aspect in order to allow the subsequent performance of a self-aligned protection operation. Because the depth of recess 160 is not a critical dimension, the formation of the recess can be done in multiple ways. Representatively, a contact of copper or a copper alloy may be over polished, or the recess can be formed by a timed wet etch (sulfuric or acetic acid based) or dry etch (using chlorine based chemistry). In one embodiment, a representative depth of recess 160 is on the order of 1 nm-1 μm.

Figure 3:
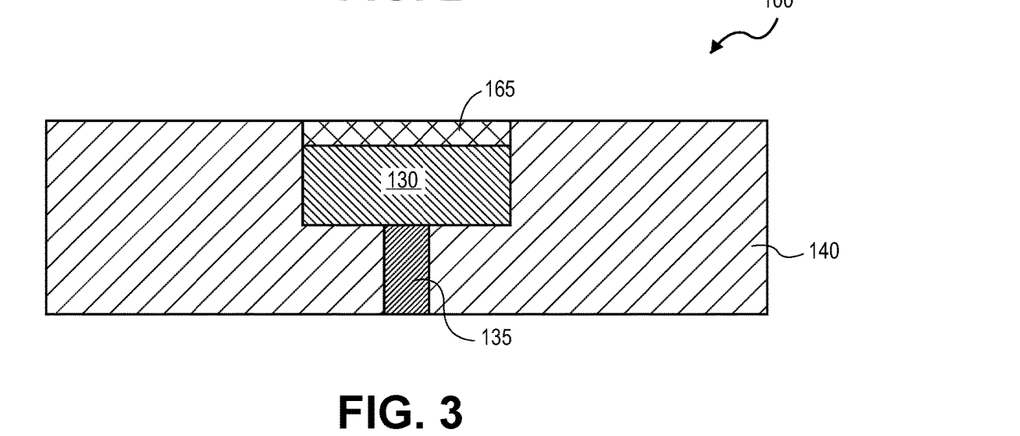
FIG. 3 shows the structure of FIG. 2 after the contact is capped by a protective dielectric layer and polished to achieve a planar surface.

FIG. 3 shows the structure of FIG. 2 after the contact metal is capped by a protective dielectric layer. In one embodiment, protective dielectric layer 165 is silicon dioxide introduced by blanket deposition and polishing. Silicon dioxide is used, in one embodiment, because it provides an etch selectivity relative to a silicon nitride for interlayer dielectric material 140 (an etch selectivity utilized in a subsequent operation). Silicon dioxide also provides a natural site for the selective attachment of nucleic acid molecules (e.g., DNA molecules) on the surface of structure 100.

Figure 4:
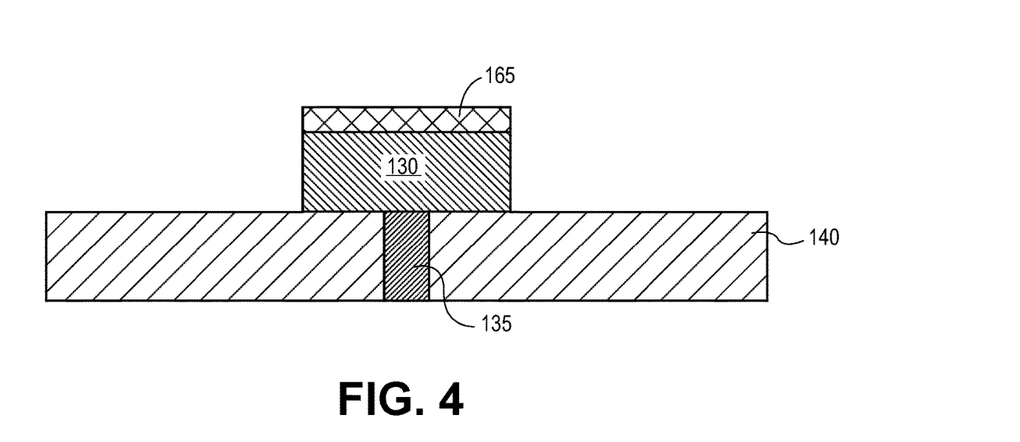
FIG. 4 shows the structure of FIG. 3 following the removal of the interlayer dielectric material around the contact.

FIG. 4 shows the structure of FIG. 3 following the removal of interlayer dielectric material 140 around contact 130. Where interlayer dielectric material is silicon nitride, a selective and timed silicon nitride dry etch may be performed to expose the sidewalls of contact 130. Depending on the thickness of protective dielectric layer 165 used and any liner used for the metal layer (contact 130), various fluorine-based chemistries (e.g., $CHF_3$, $SF_6$) can be used. Protective dielectric layer 165 serves as a self-aligned hard mask. The depth of the etch will determine the depth of the electrodes, and the exact depth is not critical to a first order, hence there is no need for an etch stop layer, and a timed etch should be sufficient. Also, the directionality of the etch is not critical as the etch can be made selective. Uniformity across a wafer is preferred, but again not critical for the current application, and some variation (e.g., five percent variation) is tolerable.

Figure 5:
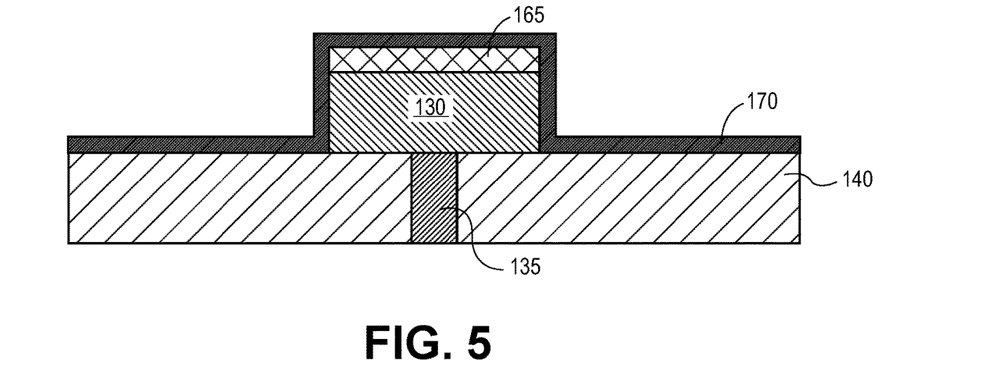
FIG. 5 shows the structure of FIG. 4 after a conformal deposition of a first electrochemical electrode layer on the structure.

FIG. 5 shows the structure of FIG. 4 after a blanket deposition of a first electrochemical electrode layer (referred to herein as "bottom electrode"). In one embodiment, the introduction of bottom electrode 170 is a conformal deposition done after any areas in which there are peripheral circuitry or bond pads are protected with a sacrificial material such as a photoresist (not shown) before the deposition to be lifted off later (this liftoff has no critical dimensions and is only done to protect non-device areas of the die). A suitable electrode material for bottom electrode 170 can be gold, platinum, boron doped diamond, diamond like carbon or some other metal alloy that performs well electrochemically. Atomic layer deposition (ALD) or sputtering tools can be used for the conformal deposition depending on the material being used. Alternatively, selective electroless plating may also be used for certain materials.

Figure 6:
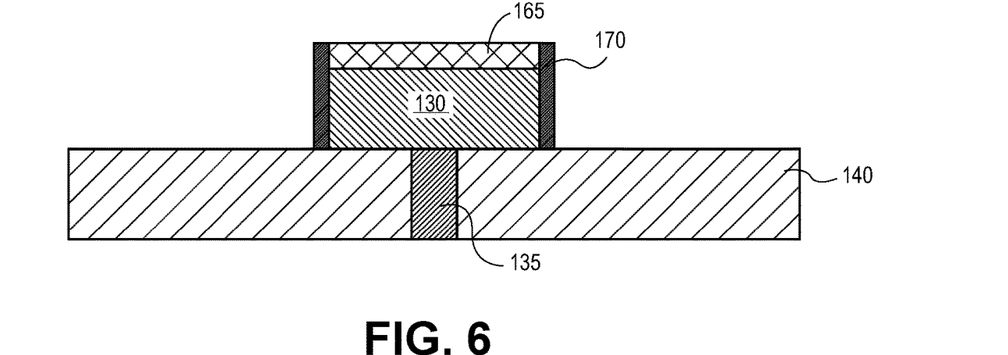
FIG. 6 shows the structure of FIG. 5 after defining the bottom electrode.

FIG. 6 shows the structure of FIG. 5 after defining the bottom electrode. Bottom electrode 170 is defined by using a directional etch to leave the electrode material on the sidewall of contact 130 and etching away the remaining material. Depending on the material used in the conformal deposition, various etch strategies can be employed in this step. If platinum or gold is used as an electrode material, an argon based sputter etch with some chlorine can be used to attain the directional etch needed. Due to the non-volatile nature of the sputter etched material, re-deposition can be a problem and the etch will have to be optimized for that. In case boron doped diamond (BDD) or doped diamond like Carbon (DLC) is used as an electrode material a high density oxygen plasma can be used to form the desired geometry. If an electroless material deposition was chosen for depositing the bottom electrode then this definition operation may be omitted.

Figure 7:
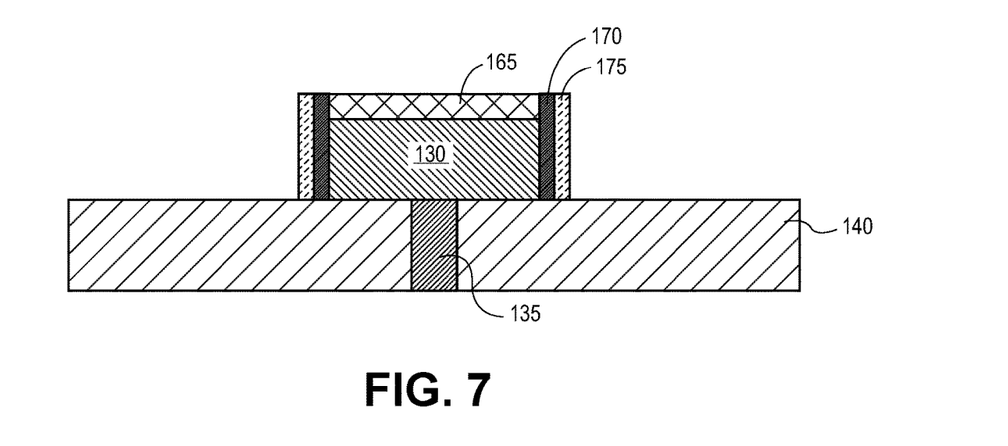
FIG. 7 shows the structure of FIG. 6 after introduction and definition of a sacrificial material on the bottom electrode.

FIG. 7 shows the structure of FIG. 6 after introduction of a sacrificial material on the bottom electrode. A thickness of a layer of sacrificial material 175 will define a gap between bottom electrode 170 and a top electrode. In one embodiment, sacrificial material 175 is chosen such that it can be etched selectively at the end of the process. Representatively, chromium and tungsten can be used as can metal oxides that can be deposited by ALD. Chromium can be etched directionally using a chlorine chemistry in a high density plasma tool. Representatively, sacrificial material 175 is deposited and defined similar to a material for bottom electrode 170. A representative thickness of sacrificial material 175 is on the order of 1 nm-300 nm.

Figure 8:
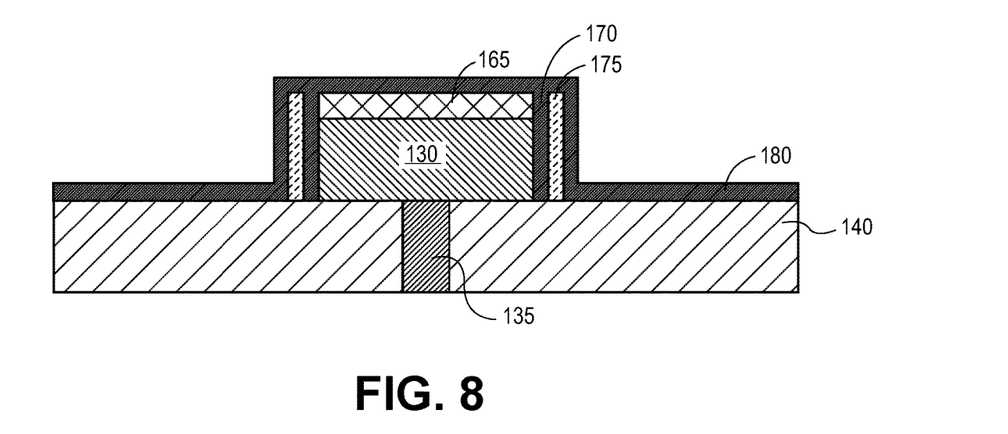
FIG. 8 shows the structure of FIG. 7 following the introduction of a top electrode on the structure.

FIG. 8 shows the structure of FIG. 7 following the introduction of a top electrode on the structure. In one embodiment, a material for top electrode 180 is deposited using a conformal deposition technique, such as sputter deposition if a metal is being used as an electrode material. In one embodiment, top electrode 180 is common to all the transducers and a contact to substrate is made at an edge of the transducer array, although connections can also be made periodically through the array (top electrode connection to the substrate is not shown). Thus, top electrode 180 is left as it is and only defined via liftoff to make sure the layer is contained in the array region of the die only. Such liftoff step does not have any tight critical dimensions. In one embodiment, a material for top electrode 180 is typically the same material used for bottom electrode 170, but can be another material depending on the electrochemical tag being used and the bias points being used for detection. Different electrode materials can exhibit different adhesion/fouling properties for reduction or oxidation of the species; hence the material can be chosen to be different than bottom electrode 170. Similar to bottom electrode 170 materials representative options for the top electrode material would be gold, platinum, boron doped diamond, diamond like carbon.

Figure 9:
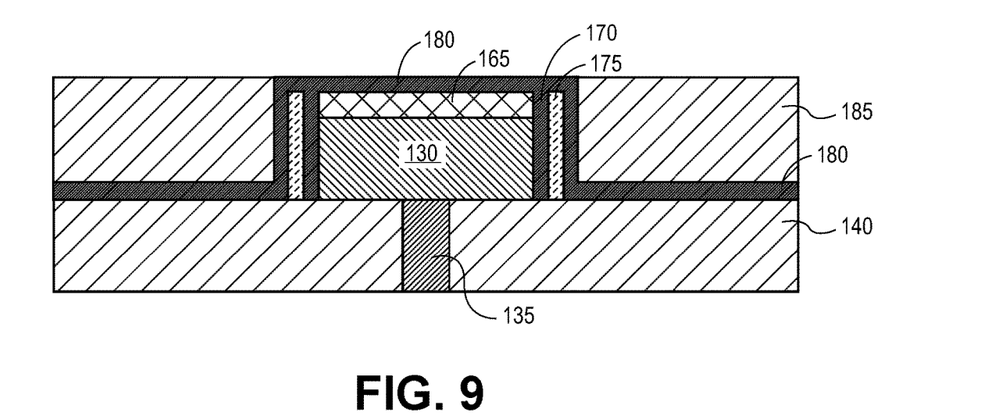
FIG. 9 shows the structure of FIG. 8 following the passivation of the structure.

FIG. 9 shows the structure of FIG. 8 following the passivation of the structure. In one embodiment, the surface is passivated to further protect the surface and limit a current between the top electrode and a reference electrode. This is done by performing a dielectric depositon and planarization of the deposited dielectric material 185. Representatively, silicon nitride (or oxynitride) is used as passivation material 185 owing to the availability of low temperature deposition tools (sub 350° C.) such as (HD)PECVD and adequate passivation properties for fluid exposure on the surface. Planarization can be done by chemical mechanical polish (CMP) using a slurry formulation that will be selective to the top electrode material (polish stop).

Figure 10:
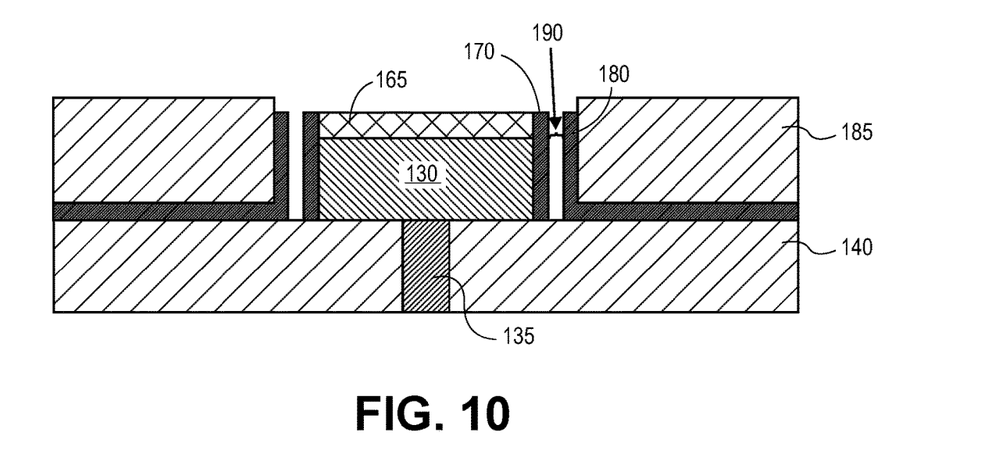
FIG. 10 shows the structure of FIG. 9 following the disconnection of top and bottom electrodes and removal of sacrificial material between the electrodes.
Figure 11:
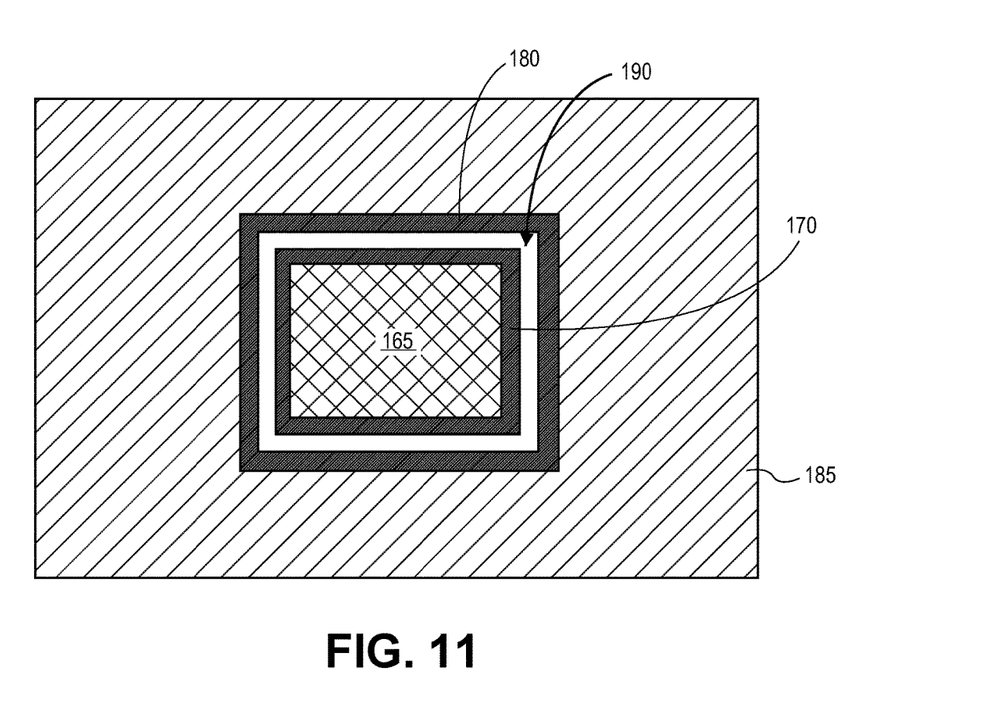
FIG. 11 shows a top view of the structure of FIG. 10 and illustrates a transducer including electrodes separated by a gap.

FIG. 10 shows the structure of FIG. 9 following the disconnection of top and bottom electrodes and removal of sacrificial material between the electrodes. In one embodiment, top electrode 180 is etched using a directional etch that electrically disconnects top electrode 180 and bottom electrode 170 so different biases can be applied to each electrode. This etch also exposes the sacrificial material which can be removed (e.g., by etching) while the die is still on the wafer or after the die is diced. Top electrode can also be disconnected as a result of a chemical mechanical polish planarization performed previously, removing the metal layer together with the dielectric. This may simplify the processing and, because the polish stop depth is not critical, a device can be designed to tolerate such a polish. Representatively, a selective wet etch can be used to etch the sacrificial material (e.g., chrome etch if chromium as sacrificial material used, warm hydrogen peroxide if tungsten used as sacrificial material). Removal of sacrificial material 175 leaves gap 190 between bottom electrode 170 and top electrode 180. FIG. 11 shows a top view of the structure of FIG. 10 and illustrates a transducer including disconnected electrodes.

Figure 12:
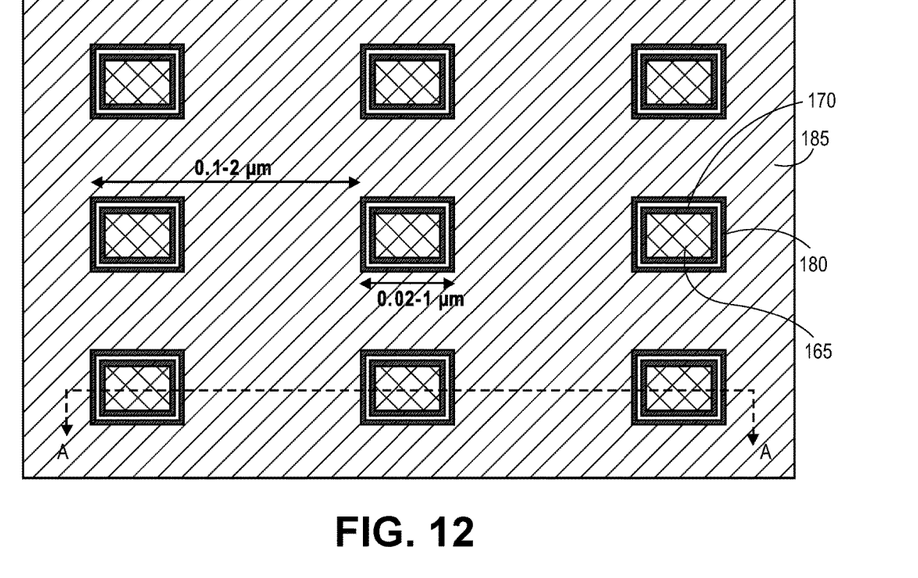
FIG. 12 shows a top view of an array of transducers on an integrated circuit structure.
Figure 13:
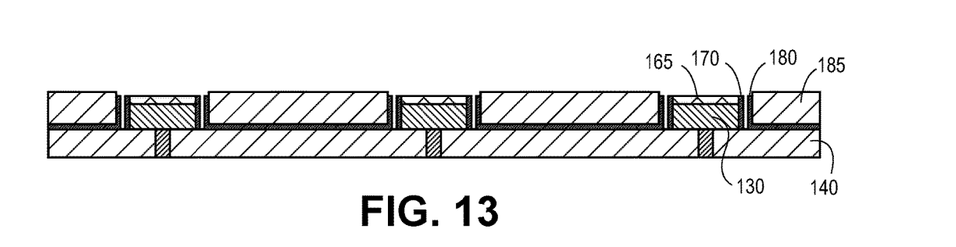
FIG. 13 shows a cross-sectional schematic through three of the devices shown in FIG. 12.

FIG. 12 shows a top view of an array of transducers on an integrated circuit structure. Representatively, one section of the array before a top electrode connection is made to the substrate will contain 1024×512 devices with device to device pitch being about 0.1 to two microns and the metal layer dimensions having the minimum allowable size determine by the backend design rules of the process being used and the stopping metal layer (e.g., 0.02 µm to 1 µm). The resulting top view schematic of such a 3×3 array of integrated transducers are shown in FIG. 12. FIG. 13 shows a cross-sectional schematic through three of the devices shown in FIG. 12.

Figure 14:
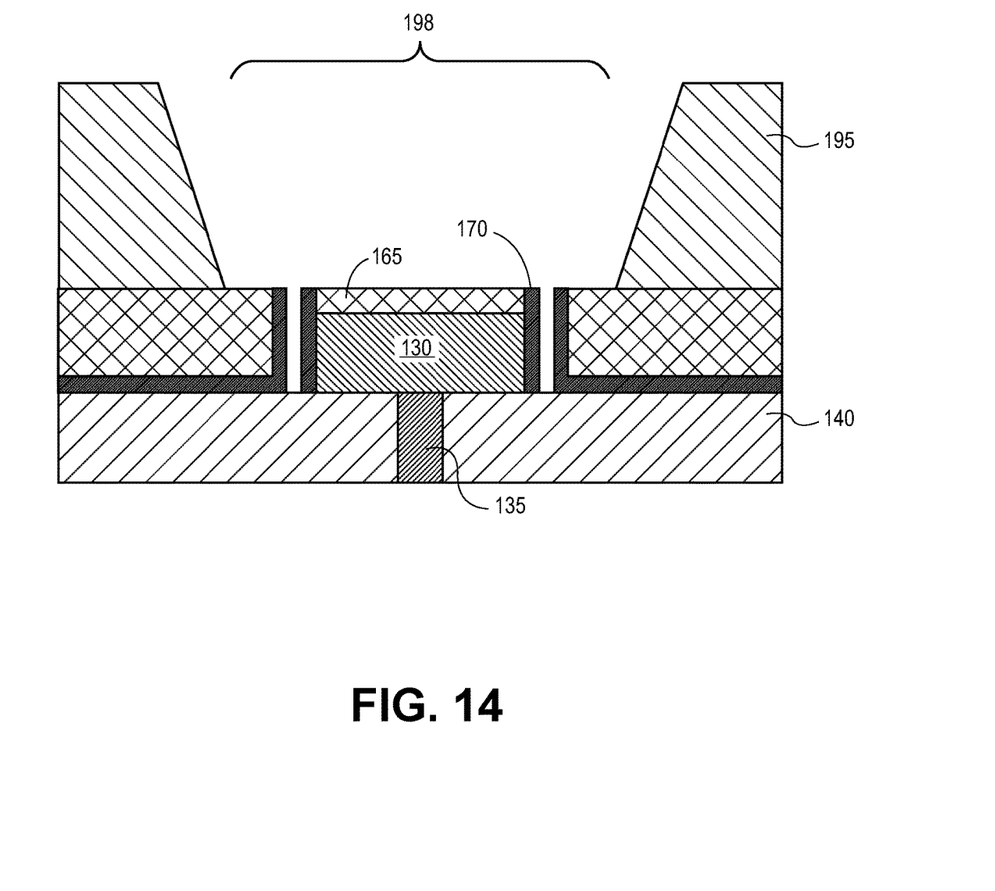
FIG. 14 shows the structure of FIG. 10 following the optional formation of a well to the transducer.

FIG. 14 shows the structure of FIG. 10 following the optional formation of a well to the transducer. FIG. 14 shows dielectric material 195 of, for example, silicon nitride introduced (deposited) on the structure and opening 198 formed in the dielectric material to expose the electrodes and define a well. Such a well may be used, in one aspect, to contain a solution including a nucleic acid for analysis.

Various modifications can be made to the process if a well has to be formed on top of the devices for forming an isolated chamber or bead attachment for example. Once such alternative device architecture can simply be accomplished by substituting oxide instead of the nitride passivation in the final passivation step and adding another nitride deposition/etch step to form a well. The cross-sectional schematic for one such alternative device structure is shown in FIG. 14.

Examples

Example 1 is an apparatus including a circuit substrate including a contact in a metal layer; and a transducer including a first electrode disposed on and coupled to a sidewall of the contact and a second electrode coupled to a conductor through which voltage can be applied, wherein the second electrode includes a profile aligned to the sidewall of the contact and separated from the first electrode by a gap.

In Example 2, the contact in the apparatus of Example 1 includes a thickness defined by two pairs of opposing sidewalls and the first electrode is coupled to each sidewall.

In Example 3, the first electrode in the apparatus of Example 2 has a height dimension relative to the thickness of the contact and the thickness of the contact is less than the height dimension of the first electrode.

In Example 4, the apparatus of Example 3 further includes a capping material on the contact, the capping material comprising a property that binds to nucleic acids.

In Example 5, the capping material in the apparatus of Example 4 includes silicon dioxide.

In Example 6, the material for the second electrode in the apparatus of any of Examples 1 and 2 is different than a material for the first electrode.

In Example 7, the apparatus of any of Examples 1 and 2 further includes a dielectric material on the metal layer, the dielectric layer including an opening to expose the transducer.

Example 8 is a method including forming a transducer adjacent a contact in a metal layer on a substrate, the transducer including a first electrode disposed on a sidewall of the contact and a second electrode coupled to a conductor through which voltage can be applied, wherein the second electrode includes a profile aligned to the sidewall of the contact and separated from the first electrode by a gap.

In Example 9, the contact in the method of Example 8 includes a thickness including a base and top defined by two pairs of opposing sidewalls and forming the transducer includes exposing the sidewalls and conformally depositing the first electrode on the contact.

In Example 10, prior to conformally depositing the first electrode on the contact, the method in Example 9 includes depositing a capping material on the top of the contact and conformally depositing the first electrode includes depositing the first electrode on the capping material.

In Example 11, prior to depositing the capping material, the method in Example 10 includes recessing the contact.

In Example 12, the method of Example 10 further includes removing the first electrode from the top of the contact and conformally depositing a sacrificial material on the first electrode.

In Example 13, the method of Example 12 further includes conformally depositing the second electrode on the sacrificial material and the contact and, after depositing the second electrode, removing the sacrificial material.

In Example 14, the method of Example 12 further includes depositing a dielectric material on the substrate and forming an opening to the transducer.

In Example 15, the nucleic acid sequencing platform is formed by the method of any of Examples 8-12.

Example 16 is an apparatus including an integrated circuit substrate including a plurality of circuits defined by transistor devices coupled through metal lines, wherein a metal line on the substrate includes a plurality of contacts and a transducer adjacent to each of the contacts, the transducer including a first electrode disposed on a sidewall of the contact and a second electrode coupled to a conductor through which voltage can be applied, wherein the second electrode includes a profile aligned to the sidewall of the contact and separated from the first electrode by a gap.

In Example 17, each of the plurality of contacts in the apparatus of Example 16 includes a thickness defined by two pairs of opposing sidewalls and the first electrode is coupled to each sidewall.

In Example 18, each of the plurality of contacts in the apparatus of Example 17 includes a thickness dimension that is less than a height dimension of the first electrode.

In Example 19, the apparatus of Example 18 further includes a capping material on each of the plurality of contacts, the capping material including a property that binds to nucleic acids.

In Example 20, the capping material in the apparatus of Example 19 includes silicon dioxide.

In Example 21, the material for the second electrode in the apparatus of any of Examples 16 and 17 is different than a material for the first electrode.

In Example 22, the apparatus of any of Examples 16 and 17 further includes a dielectric material on the metal line, the dielectric layer including openings that expose respective ones of the transducers.

In the description above, for the purposes of explanation, numerous specific details have been set forth in order to provide a thorough understanding of the embodiments. It will be apparent however, to one skilled in the art, that one or more other embodiments may be practiced without some of these specific details. The particular embodiments described are not provided to limit the invention but to illustrate it. The scope of the invention is not to be determined by the specific examples provided above but only by the claims below. In other instances, well-known structures, devices, and operations have been shown in block diagram form or without detail in order to avoid obscuring the understanding of the description. Where considered appropriate, reference numerals or terminal portions of reference numerals have been repeated among the figures to indicate corresponding or analogous elements, which may optionally have similar characteristics.

It should also be appreciated that reference throughout this specification to "one embodiment", "an embodiment", "one or more embodiments", or "different embodiments", for example, means that a particular feature may be included in the practice of the invention. Similarly, it should be appreciated that in the description various features are sometimes grouped together in a single embodiment, figure, or description thereof for the purpose of streamlining the disclosure and aiding in the understanding of various inventive aspects. This method of disclosure, however, is not to be interpreted as reflecting an intention that the invention requires more features than are expressly recited in each claim. Rather, as the following claims reflect, inventive aspects may lie in less than all features of a single disclosed embodiment. Thus, the claims following the Detailed Description are hereby expressly incorporated into this Detailed Description, with each claim standing on its own as a separate embodiment of the invention.

What is claimed is:

1. An apparatus comprising:
   a circuit substrate comprising a contact in a metal layer; and
   a transducer comprising a first electrode disposed on and coupled to a sidewall of the contact and a second electrode coupled to a conductor through which voltage can be applied, wherein the second electrode comprises a profile aligned to the sidewall of the contact and separated from the first electrode by a gap.

2. The apparatus of claim 1, wherein the contact comprises a thickness defined by two pairs of opposing sidewalls and the first electrode is coupled to each sidewall.

3. The apparatus of claim 2, wherein the first electrode has a height dimension relative to the thickness of the contact and the thickness of the contact is less than the height dimension of the first electrode.

4. The apparatus of claim 3, further comprising a capping material on the contact, the capping material comprising a property that binds to nucleic acids.

5. The apparatus of claim 4, wherein the capping material comprises silicon dioxide.

6. The apparatus of claim 1, wherein a material for the second electrode is different than a material for the first electrode.

7. The apparatus of claim 1, further comprising a dielectric material on the metal layer, the dielectric layer comprising an opening to expose the transducer.

8. A method comprising:
   forming a transducer adjacent a contact in a metal layer on a substrate, the transducer comprising a first electrode disposed on a sidewall of the contact and a second electrode coupled to a conductor through which voltage can be applied, wherein the second electrode comprises a profile aligned to the sidewall of the contact and separated from the first electrode by a gap.

9. The method of claim 8, wherein the contact comprises a thickness comprising a base and top defined by two pairs of opposing sidewalls and forming the transducer comprises exposing the sidewalls and conformally depositing the first electrode on the contact.

10. The method of claim 9, wherein prior to conformally depositing the first electrode on the contact, the method comprises depositing a capping material on the top of the contact and conformally depositing the first electrode comprises depositing the first electrode on the capping material.

11. The method of claim 10, wherein prior to depositing the capping material, the method comprises recessing the contact.

12. The method of claim 10, further comprising removing the first electrode from the top of the contact and conformally depositing a sacrificial material on the first electrode.

13. The method of claim 12, further comprising conformally depositing the second electrode on the sacrificial material and the contact and, after depositing the second electrode, removing the sacrificial material.

14. The method of claim 12, further comprising depositing a dielectric material on the substrate and forming an opening to the transducer.

15. A nucleic acid sequencing platform formed by the method of claim 8.

16. An apparatus comprising:
   an integrated circuit substrate comprising a plurality of circuits defined by transistor devices coupled through metal lines, wherein a metal line on the substrate comprises a plurality of contacts and a transducer adjacent to each of the contacts, the transducer comprising a first electrode disposed on a sidewall of the contact and a second electrode coupled to a conductor through which voltage can be applied, wherein the second electrode comprises a profile aligned to the sidewall of the contact and separated from the first electrode by a gap.

17. The apparatus of claim 16, wherein each of the plurality of contacts comprise a thickness defined by two pairs of opposing sidewalls and the first electrode is coupled to each sidewall.

18. The apparatus of claim 17, wherein each of the plurality of contacts comprises a thickness dimension that is less than a height dimension of the first electrode.

19. The apparatus of claim 18, further comprising a capping material on each of the plurality of contacts, the capping material comprising a property that binds to nucleic acids.

20. The apparatus of claim 19, wherein the capping material comprises silicon dioxide.

21. The apparatus of claim 16, wherein a material for the second electrode is different than a material for the first electrode.

22. The apparatus of claim 16, further comprising a dielectric material on the metal line, the dielectric layer comprising openings that expose respective ones of the transducers.

* * * * *